United States Patent [19]

Peet et al.

[11] Patent Number: 4,526,979

[45] Date of Patent: Jul. 2, 1985

[54] CARBAMATES AND OXALAMIDES OF AMINO-N-(1H-TETRAZOL-5-YL)BENZAMIDES

[75] Inventors: Norton P. Peet; Shyam Sunder, both of Indianapolis, Ind.

[73] Assignee: Merrell Dow Pharmaceuticals Inc., Cincinnati, Ohio

[21] Appl. No.: 517,085

[22] Filed: Jul. 22, 1983

[51] Int. Cl.$^3$ ............................................. C07D 257/06
[52] U.S. Cl. .................................................... 548/251
[58] Field of Search ........................................ 548/251

[56] References Cited

U.S. PATENT DOCUMENTS 3,824,249 6/1974 Regnier et al. ................... 548/251
4,176,631 3/1979 Ford et al. ......................... 548/251

OTHER PUBLICATIONS

Moffett et al., J. Med. Chem., 14(10), pp. 963–968 (1971).

Primary Examiner—Glennon H. Hollrah
Assistant Examiner—D. B. Springer
Attorney, Agent, or Firm—John J. Kolano; Gary D. Street; Raymond A. McDonald

[57] ABSTRACT

Alkoxycarbonyl and oxalyl derivatives of amino-N-(1H-tetrazol-5-yl)benzamides are described herein. The compounds involved are useful as antiallergic agents. These compounds can be prepared by the reaction of an amino-N-(1H-tetrazol-5-yl)benzamide with an appropriate acid chloride.

9 Claims, No Drawings

CARBAMATES AND OXALAMIDES OF AMINO-N-(1H-TETRAZOL-5-YL)BENZAMIDES

The present invention relates to amide derivatives of amino-N-(1H-tetrazol-5-yl)benzamides. More particularly, it relates to aminobenzamides of the type referred to above wherein the amino group is substituted by an alkoxy carbonyl group or by an oxalyl ester group. Thus, the present invention is directed to compounds having the following general formula:

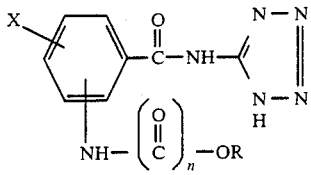

wherein n is 1 or 2; X is hydrogen or chlorine; and R is alkyl of 1-6 carbon atoms; and the pharmaceutically acceptable salts thereof.

In the above benzamide structure, the amine substituent can be in any isomeric position on the phenyl ring with respect to the carboxamide. Thus, the amine group can be ortho, meta or para with respect to the carboxamide. Examples of the alkyl group referred to above are methyl, ethyl, propyl, butyl, isobutyl and hexyl with methyl and ethyl being preferred.

Equivalent for the purposes of this invention are the pharmaceutically acceptable salts and also the hydrates of the compounds and their salts. The term "pharmaceutically acceptable salts" as used herein is intended to include non-toxic cationic salts such as the alkali metal salts, e.g., sodium and potassium; alkaline earth metal salts such as calcium, magnesium or barium; salts with ammonia; and salts with organic bases, e.g., amines such as triethylamine, n-propylamine and tri-n-butylamine.

While certain of the amides above have been referred to as oxalyl substituted compounds because of their relationship to oxalic acid, they can also be named systematically as substituted 2-oxoglycine alkyl esters and this nomenclature is used for the compounds in the examples below.

The compounds of the present invention are prepared by the reaction of a 2-aminobenzamide of the formula:

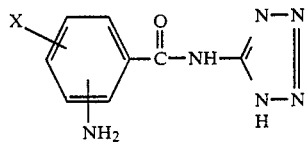

wherein X is defined as above, with an acid chloride of the formula:

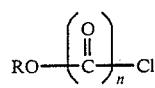

wherein n and R are defined as above. The reaction is carried out in an inert solvent such as dimethylformamide. Although the reaction does take place without the application of external heat and, depending on the specific reactants, may in fact be exothermic, the mixture is generally heated to ensure completion of the reaction. The product is isolated from the reaction mixture by standard procedures and, when dimethylformamide is used as the solvent, this consists of diluting the mixture with water and then cooling it.

In an alternate procedure for preparing the compounds of the present invention, the aminobenzamides shown above can be reacted with a strong base, such as sodium ethoxide, and an appropriate dicarboxylic acid alkyl ester, such as ethyl oxalate or ethyl carbonate.

The aminobenzamides used as the starting material in the above process are obtained by catalytic hydrogenation of a solution of the appropriate nitrobenzamide. The preferred catalyst is 5% Pd/C although similar catalysts, such as Pt/C, can also be used. Depending on the specific compound involved, the starting tetrazole can be dissolved in aqueous 1 N sodium hydroxide solution and, if necessary, this can be diluted with ethanol or additional water. Alternatively, the reduction can be carried out in acetic acid solution.

The necessary nitrobenzamide is obtained from the appropriate nitrobenzoyl chloride by reaction with 5-aminotetrazole and the necessary acid chloride is obtained from the corresponding carboxylic acid, with standard procedures used for both reactions.

The compounds obtained above are converted to the pharmaceutically acceptable salts by reacting the tetrazole final product with a substantially equimolar amount of the appropriate base in an aqueous solution or in a suitable organic solvent such as methanol or ethanol. The salts are recovered by standard methods such as filtration if they are insoluble in the original medium, or, if they are soluble in that medium, the salt is precipitated by evaporation of the solvent or by addition of a non-solvent for the salt.

The compounds of the present invention possess antiallergic activity. Thus, they are useful in the treatment of conditions in which antigen-antibody reactions are responsible for disease and particularly in the treatment of allergic diseases such as (but not limited to) extrinsic asthma, hay fever, urticaria, eczema or atopic dermititis and upper respiratory conditions such as allergic rhinitis.

The compounds of the present invention may be administered either as individual therapeutic agents or as mixtures with other therapeutic agents. They may be administered alone but are generally administered in the form of pharmaceutical compositions, i.e., mixtures of the active agents with suitable pharmaceutical carriers or diluents. Examples of such compositions include aerosol sprays, aqueous or oily suspensions and aqueous solutions for injection. The present compounds can be used in the same general way as disodium cromoglycate For parenteral administration or inhalation, solutions or suspensions of a compound of the present invention with conventional pharmaceutical vehicles may be employed, e.g., as an aerosol spray for inhalation, as an aqueous solution for intravenous injection or an oily suspension for intramuscular injection. The compounds may also be administered by means of inhalers or other devices which permit the active compounds in the form of dry powders to come into direct contact with the lungs. The indicated compositions can be prepared by known techniques as described in standard texts such as *Remington's Pharmaceutical Sciences*, Mack Publishing Company, Easton, Pennsylvania.

The antiallergic activity of the present compounds is demonstrated by the IgE mediated rat Passive Cutaneous Anaphylaxis (PCA) test. This test is generally accepted as one of the best animal models for the qualitative determination of antiallergic activity. Disodium cromoglycate is active in this test when administered i.p. but not orally. The method can be described briefly as follows:

PCA Test Method

1. Antisera—Various standard methods described in the literature were used for the preparation of reaginic antisera to ovalbumin in either Hooded Lister or Brown Norway adult rats.

2. Animals—Adult male Sprague-Dawley or female Wistar Kyoto rats were used as antisera recipients in the test. The animals were allowed to acclimate for 5–14 days with food and water ad lib.

3. Sensitization—Recipient rats were passively sensitized by the intradermal injection of 100 microliters of two dilutions of antiserum (one injection on each side of the back). Sensitization occurred 48–72 hours prior to antigen challenge.

4. Administration of Test Compound—Four to six animals were used for each test compound/dilution. Compounds were homogenized in an appropriate carrier solution, and administered i.p. at 60 mg/kg 5 minutes prior to challenge.

5. Antigen Challenge and Reaction Evaluation—Ovalbumin (0.1–1.0 mg in a 0.5% solution of Evan's Blue dye) in saline was given to each rat by i.v. administration. Thirty minutes later, the resultant PCA reactions were measured for average diameter and color intensity from the reflected surface of the skin. Test compound activity is expressed as percent inhibition based on control reactions. When tested by the above procedure, the compounds of the present invention were active intraperitoneally.

The following examples are presented to illustrate the present invention but they should not be construed as limiting it in any way.

EXAMPLE 1

To a solution of 10.3 g of 5-aminotetrazole monohydrate in 300 ml of tetahydrofuran and 15 ml of water was added 9.3 g of 2-nitrobenzoyl chloride. The solution was allowed to stand for 30 minutes before it was diluted with 200 ml of water and stored in a refrigerator for 72 hours. The solid which formed was separated by filtration to give 2-nitro-N-(1H-tetrazol-5-yl)-benzamide melting at about 272°–273° C. with decomposition.

In a similar manner, a solution of 46.4 g of 3-nitrobenzoyl chloride in 100 ml of tetrahydrofuran was added to a hot solution of 51.6 g of 5-aminotetrazole monohydrate in 1200 ml of tetrahydrofuran and 50 ml of water. The mixture was allowed to stand for 16 hours and then concentrated, and the resulting slurry was treated with water. The white solid was collected, washed with water and oven-dried to give 3-nitro-N-(1H-tetrazol-5-yl)benzamide melting at about 276° C. with decomposition.

Similarly, a solution of 109 g of 2-chloro-3-nitrobenzoyl chloride in 100 ml of tetrahydrofuran was reacted with a mixture of 103 g of 5-aminotetrazole monohydrate in 1200 ml of hot tetrahydrofuran and 50 ml of water. A voluminous precipitate appeared and, after 1 hour, the mixture was diluted with 2 liters of water and the resulting white solid was collected and oven-dried to give 2-chloro-3-nitro-N-(1H-tetrazol-5-yl)-benzamide melting at about 279° C. with decomposition. In this case, the indicated acid chloride was obtained by the reaction of 2-chloro-3-nitrobenzoic acid with phosphorus pentachloride in cyclohexane. The acid chloride melts at about 57°–59° C.

4-Chloro-3-nitro-N-(1H-tetrazol-5-yl)benzamide, melting at about 278° C. with decomposition, was obtained from 4-chloro-3-nitrobenzoic acid by following the same procedure described above for the 2-chloro compound.

EXAMPLE 2

A solution was prepared from 19 g of 2-nitro-N-(1H-tetrazol-5-yl)benzamide in 100 ml of aqueous 1 N sodium hydroxide and 100 ml of ethanol. A 0.5-gram quantity of 5% Pd/C catalyst was added and the mixture was hydrogenated in a Parr apparatus at 1520 mm Hg pressure until uptake of hydrogen stopped. The catalyst was removed by filtration and the filtrate was treated with aqueous 1 N hydrochloric acid. The white solid which formed was separated by filtration and dried to give 2-amino-N-(1H-tetrazol-5-yl)benzamide melting at about 253°–254° C.

EXAMPLE 3

A slurry of 10 g of 3-nitro-N-(1H-tetrazol-5-yl)-benzamide and 250 ml of 70% acetic acid was treated with 1 g of 10% Pd/C and hydrogenated in a Parr apparatus at about 2550 mm Hg for 2.5 hours. The mixture was then filtered to separate the white solid and catalyst. The mixture of solids obtained was slurried with 250 ml of hot dimethylformamide and filtered. The resulting filtrate was diluted slowly with 250 ml of water and the resulting warm solution was filtered to remove a small amount of gelatinous material. The yellow crystalline solid which formed in the filtrate on cooling was separated by filtration and oven-dried to give 3-amino-N-(1H-tetrazol-1-yl)benzamide melting at about 281° C. with decomposition.

When the above procedure was repeated using the appropriate starting materials and a hydrogenation period of 6.5 hours, the following compounds were obtained:

3-Amino-2-chloro-N-(1H-tetrazol-5-yl)benzamide melting at about 293° C. with decomposition.

3-Amino-4-chloro-N-(1H-tetrazol-5-yl)benzamide melting at about 268° C. with decomposition.

EXAMPLE 4

To a solution of 5.0 g of 2-amino-N-(1H-tetrazol-5-yl)benzamide in 20 ml of dimethylformamide was added 2.3 g of methyl chloroformate. The resulting solution was warmed for 2 hours and then diluted with a small volume of water. The solid which formed on cooling was separated by filtration to give [2-((1H-tetrazol-5-yl)-aminocarbonyl)phenyl]carbamic acid methyl ester melting at about 236°–237° C. after recrystallization from ethanol.

EXAMPLE 5

When the procedure of Example 4 was repeated using the appropriate starting materials, the following compounds were obtained:

[2-((1H-Tetrazol-5-yl)aminocarbonyl)phenyl]carbamic acid ethyl ester melting at about 221°–223° C. after recrystallization from a mixture of dimethylformamide and water.

[3-((1H-Tetrazol-5-yl)aminocarbonyl)phenyl]carbamic acid methyl ester melting at about 266°–267° C.

after recrystallization from a mixture of dimethylformamide and water.

[3-((1H-Tetrazol-5-yl)aminocarbonyl)phenyl]carbamic acid ethyl ester melting at about 268°-268.5° C. with decomposition.

EXAMPLE 6

To a solution of 2.3 g of sodium and 200 ml of ethanol was added 5.1 g of 2-amino-N-(1H-tetrazol-5-yl)benzamide and 11.0 g of diethyl oxalate. The resulting solution was heated at 50° C. for 20 hours and then acidified with glacial acetic acid. The clear acid solution obtained was diluted with water and the solid which formed was separated by filtration, washed with water and air-dried to give 2-oxo-N-[2-((1H-tetrazol-5-yl)aminocarbonyl)phenyl]glycine ethyl ester melting at about 231°-232° C.

EXAMPLE 7

To a warm solution of 6.0 g of 3-amino-N-(1H-tetrazol-1-yl)benzamide in 60 ml of dimethylformamide was added 3.7 g of methyl oxalyl chloride. After a few minutes, a precipitate appeared. The mixture was then heated and the solution which resulted was diluted with 5 ml of water and allowed to cool. The solid which formed was separated by filtration to give 2-oxo-N-[3-((1H-tetrazol-5-yl)aminocarbonyl)phenyl]glycine methyl ester melting at about 253°-253.5° C. with decomposition after recrystallization from a mixture of dimethylformamide and water.

EXAMPLE 8

The procedure of Example 7 was repeated using other amino-N-(1H-tetrazol-5-yl)benzamides and appropriate alkyl oxalyl chlorides. The reaction conditions used were generally similar to those described above. The following compounds were obtained:

2-Oxo-N-[3-((1H-tetrazol-5-yl)aminocarbonyl)phenyl]glycine ethyl ester melting at about 260°-261° C. with decomposition.

2-Oxo-N-[2-chloro-3-((1H-tetrazol-5-yl)aminocarbonyl)phenyl]glycine methyl ester melting at about 261° C. with decomposition.

2-Oxo-N-[2-chloro-3-((1H-tetrazol-5-yl)aminocarbonyl)phenyl]glycine ethyl ester melting at about 280° C. with decomposition.

2-Oxo-N-[6-chloro-3-((1H-tetrazol-5-yl)aminocarbonyl)phenyl]glycine methyl ester melting at about 211°-213° C. with decomposition. In this case, only a small amount of solid was obtained by the initial addition of water and it was necessary to dilute the solution with a relatively large volume of water in order to obtain the indicated product.

2-Oxo-N-[6-chloro-3-((1H-tetrazol-5-yl)aminocarbonyl)phenyl]glycine ethyl ester melting at about 201°-204° C. with decomposition. In this instance, it was again necessary to dilute the solution with a larger volume of water in order to be able to isolate the indicated product.

2-Oxo-N-[4-((1H-tetrazol-5-yl)aminocarbonyl)phenyl]glycine methyl ester melting at about 257°-257.5° C. with decomposition, after recrystallization from a mixture of dimethylformamide and water.

2-Oxo-N-[4-((1H-tetrazol-5-yl)aminocarbonyl)phenyl]glycine ethyl ester melting at about 273° C. with decomposition, after recrystallization from 2-methoxyethanol. In this case, the reaction mixture was poured into a large volume of water before the product was isolated.

What is claimed is:

1. A compound of the formula:

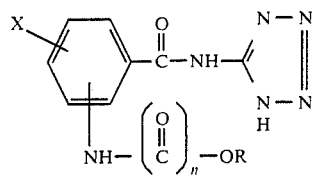

wherein n is 1 or 2; X is hydrogen or chlorine; and R is alkyl of 1-6 carbon atoms; and the pharmaceutically acceptable salts thereof.

2. A compound according to claim 1 which has the formula:

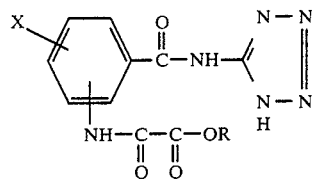

wherein X is hydrogen or chlorine; and R is alkyl of 1-6 carbon atoms; and the pharmaceutically acceptable salts thereof.

3. A compound according to claim 1 which has the formula:

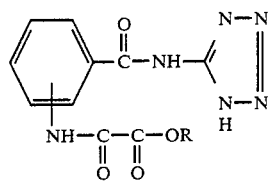

when R is alkyl of 1-6 carbon atoms; and the pharmaceutically acceptable salts thereof.

4. A compound according to claim 1 which is 2-oxo-N-[2-((1H-tetrazol-5-yl)aminocarbonyl)phenyl]glycine ethyl ester.

5. A compound according to claim 1 which is 2-oxo-N-[3-((1H-tetrazol-5-yl)aminocarbonyl)phenyl]glycine ethyl ester.

6. A compound according to claim 1 which is 2-oxo-N-[4-((1H-tetrazol-5-yl)aminocarbonyl)phenyl]glycine ethyl ester.

7. A compound according to claim 1 which has the formula:

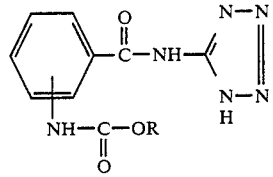

wherein R is alkyl of 1-6 carbon atoms; and the pharmaceutically acceptable salts thereof.

8. A compound according to claim 1 which is [2-((1 H-tetrazol-5-yl)aminocarbonyl)phenyl]carbamic acid ethyl ester.

9. A compound according to claim 1 which is [3-((1H-tetrazol-5-yl)aminocarbonyl)phenyl]carbamic acid ethyl ester.

* * * * *